United States Patent [19]

Olivier

[11] Patent Number: 5,017,727
[45] Date of Patent: May 21, 1991

[54] POLYMERIZABLE ANTIOXIDANT COMPOSITION

[75] Inventor: Errol J. Olivier, Baton Rouge, La.

[73] Assignee: Copolymer Rubber & Chemical Corporation, Baton Route, La.

[21] Appl. No.: 550,373

[22] Filed: Jul. 10, 1990

[51] Int. Cl.$^5$ .............................................. C07C 39/17
[52] U.S. Cl. ..................... 568/719; 568/23; 568/25; 568/61; 568/67; 568/721; 568/733; 568/734
[58] Field of Search .............. 568/719, 721, 733, 734, 568/58, 61, 67, 23, 25

[56] References Cited

U.S. PATENT DOCUMENTS

| | | | |
|---|---|---|---|
| 3,317,466 | 5/1967 | Cadwell et al. | 568/719 |
| 3,320,210 | 5/1967 | Cadwell et al. | 568/719 |
| 3,326,854 | 6/1967 | Jackson, Jr. et al. | 568/719 |
| 3,517,071 | 6/1970 | Cadwell et al. | 568/719 |
| 3,663,602 | 5/1972 | Steinman | 568/719 |

FOREIGN PATENT DOCUMENTS

| | | | |
|---|---|---|---|
| 13248 | 7/1967 | Japan | 568/721 |
| 477153 | 7/1972 | U.S.S.R. | 568/719 |

*Primary Examiner*—Werren B. Lone
*Attorney, Agent, or Firm*—Rockey and Rifkin

[57] ABSTRACT

This invention is addressed to antioxidants which are polymerizable using the Ziegler catalyst system. The antioxidant of the present invention has the formula:

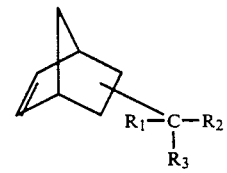

wherein $R_1$ and $R_2$ are each aryl groups containing a hindered antioxidant structure imparting antioxidant properties to the compounds. The compounds of the present invention are useful in the polymerization of olefin compounds using Ziegler catalyst systems whereby the antioxidant of the invention becomes chemically bound to the polymer while, at the same time, imparting antioxidant properties thereto.

8 Claims, No Drawings

POLYMERIZABLE ANTIOXIDANT COMPOSITION

BACKGROUND OF THE INVENTION

This invention relates to antioxidants which can be polymerized with other monomers to form copolymers imparting antioxidant properties to the polymers and to antioxidants and methods for their preparation for use in preparing such polymers.

It is well known that unsaturated monomers can be polymerized using free radical initiators. However, such free radical polymerization cannot be used in forming polymers of some monomers including propylene, butene and isobutylene. It is well known when attempts are made to polymerize such monomers with free radical catalysts or initiators, only low molecular weight polymers can be produced.

The development of the now well known Ziegler catalyst system has made it possible to polymerize such olefins to highly useful polymers and copolymers. One of the principal drawbacks to the Ziegler catalyst system is that it cannot be used with monomers containing functional groups which are polar in nature. As a general rule, such polar functional groups have a tendency to react irreversibly with components of the Ziegler catalyst system, thereby lowering the true concentration of the Ziegler catalyst components.

Equally well known is the fact that virtually all polyolefins require stabilization against uncontrolled oxidation which has a tendency to cause undesirable changes in the poly including chain scission, cross-linking and discoloration, and thus, adversely changing the mechanical and physical properties of the polymer. Extensive research has been undertaken in the area of stabilization, and that research has resulted in the development of a number of antioxidants which impart greater stability to olefin polymers, including elastomeric olefin polymers. A major class of antioxidants which has been developed over the years is the class of hindered phenols.

While molecular antioxidants such as the hindered phenols have achieved wide spread use in the stabilization of a wide variety of polyolefins, they have a tendency under certain conditions of use to migrate out of the polymer which results in the depletion of the antioxidant in the polymer, and consequently the polymer has a tendency to be degraded through oxidation. The use of bound antioxidants which remain in the polymer under conditions which promote the migration of molecular antioxidants has been advocated by (1) Kline, R. H., and Miller, J. P., "Preparation and Activity of Polymerizable Antioxidants for Emulsion Rubbers," Rubber Chemistry and Technology, 46, 96 (1973); (2) Meyer, G. E., Kavc , an "Emulsion Rubbers Copolymerized with Monomeric Antioxidants," Rubber Chemistry and Technology, 46, 106 (1973); (3) Horvath, J.W., "Bound Antioxidant Stabilized NBR in Automotive Applications," Elastomerics, August, 1979, page 19; (4) Kuczkowski, J. A., and Gillick, J. G., "Polymer-Bound Antioxidants," Rubber Chemistry and Technology, 57, 621 (1984); (5) Engels, H. W., et al, "Effectiveness of New Alkyl-Aryl-p-Phenylenediamines Which Can Be Chemically Bound to Polymers - Model Study," Rubber Chemistry and Technology, 62, 609 (1989); (6) Parker, D. K., and Schulz, G. 0., "N-(4-Anilinophenyl)-Methacrylamide, A Polymerizable Amine Antioxidant: Synthesis, Copolymerization, Copolymer Properties, and Performance," Rubber Chemistry and Technology, 62, 732 (1989); (7) Gandek, T. P., Hatton, T. A., and Reid, R. C., "Batch Extraction with Reaction: Phenolic Antioxidant Migration from Polyolefins to Water. 2. Experimental Results and Discussion," Ind. Eng. Chem. Res., 28, 1036 (1989; and (8) Miller, D. E., et al, "Persistent Antioxidants for Polymers Contacting Extractive Media," Rubber World, August 1989, page 13. Such antioxidants are characterized as polymer-bound by reason of the fact that they are chemically attached to the polymer either by way of a grafting reaction or by copolymerization with the olefinic monomers during the production of the polymer itself.

Polymer-bound antioxidants which ar copolymerized with the other monomers have been generally limited to free radical polymerizations, particularly the free radical emulsion copolymerization of butadiene and acrylonitrile in the production of NBR rubbers. Typical polymer-bound antioxidant monomers include amide or ester derivatives of acrylic or methacrylic acid which can be copolymerized by way of a free radical mechanism of the butadiene and acrylonitrile. While such polymer-bound antioxidants are well suited as monomers in free radical polymerization techniques, they are unsuitable for use in polymerizations catalyzed by the Ziegler catalyst system because their polar groups tend to act as catalyst poisons.

It has been proposed in U.S. Pat. Nos. 3,748,316; 3,796,687 and 4,017,669 to incorporate by copolymerization polar monomers using a Ziegler catalyst system. Specifically, those prior patents suggest certain norbornene compounds having a phenolic group chemically bound thereto as monomers for copolymerization with ethylene and propylene by way of a Ziegler catalyst system. The general teachings of those references include a compound said to have the following general structure:

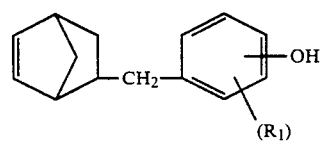

where $R_1$ is either R or OR and R can be alkyl, aryl, or cycloalkyl containing 1-18 carbon atoms, or hydrogen.

The teachings of the three patents do not describe any technique by which compounds of that type can be prepared, nor do they describe a polymerization with such a monomer. Therefore, the three patents fail to place those compounds in the possession of the public. It is also important to note that these patents overcome the poisoning effect of polar groups by using an equal molar quantity of aluminum alkyl to polar monomer, a very expensive solution, as well as impractical in view of environmental and purity standards of today's rubber and plastics industry. Furthermore, no recognition is given to the potential for the phenolic type molar monomer to impart antioxidant properties to the polar copolymer obtained therefrom.

U.S. Pat. No. 4,301,306 describes norbornenyl monophenolic compounds of the general structure shown below:

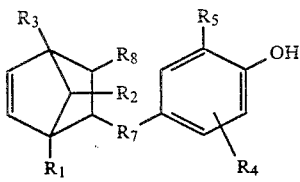

as having a reactive double bond and thereby being polymerizable. This patent teaches neither how to use the reactive norbornenyl phenolic compound in polymerization reactions, nor does it demonstrate that once polymerized, the copolymer thus obtained possesses antioxidant properties.

Norbornenyl monophenolic compounds described above were the subject of U.S. Pat. No. 4,355,148 where a ring opening polymerization using a metathesis catalyst produced a polymeric antioxidant composition incorporating the norbornenyl phenolic compound with dicyclopentadiene, norbornene or substituted norbornenes, and optionally an olefin such as 1-hexene.

It is accordingly an object of the present invention to provide polymerizable antioxidants and methods for their preparation whereby the polymerizable antioxidant can be copolymerized with another monomer or a mixture of monomers to impart to the resulting copolymer antioxidant properties.

It is a more specific object of the present invention to provide polymerizable antioxidant compounds which can be prepared by simple and inexpensive methods and which can be copolymerized with other monomers polymerizable by any of the well-known Ziegler processes without poisoning of the catalyst system.

The concepts of the invention reside in Ziegler-polymerizable antioxidant compounds which are in the form of a substituted norbornene in which the substituent contains one or more groups imparting to the molecular antioxidant properties. Preferred among the antioxidant-imparting substituent are hindered hydroxy-substituted aromatic groups, the most preferred being hindred alkyl-substituted phenols.

In the preferred practice of the present invention, the Ziegler-polymerizable antioxidants of the present invention are compounds having the general formula:

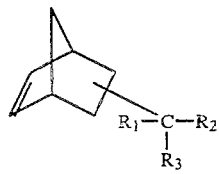

wherein $R_1$ and $R_2$ are each antioxidant-imparting substituents. In the preferred practice of the present invention, $R_1$ has the formula:

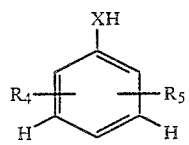

and $R_2$ has the formula:

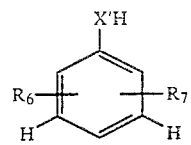

in each of the formulas, X and X' is selected from a divalent oxygen atom and a divalent sulfur; and, $R_4$, $R_5$, $R_6$, and $R_7$ are each independently alkyl containing 1-8 carbon atoms such as methyl, ethyl, propyl, isopropyl, butyl, t-butyl, pentyl, isopentyl, etc. And $R_3$ in the above structure is either hydrogen or an alkyl group containing 1-4 carbon atoms such as methyl, ethyl, propyl, etc. The only restriction on the location of groups $R_4$–$R_7$ and the chain bearing the norbornene ring is that they must occupy sites ortho and para to the oxygen or sulfur atom in the aromatic ring.

Preferred among the foregoing substituted norbornenes are the following compounds:

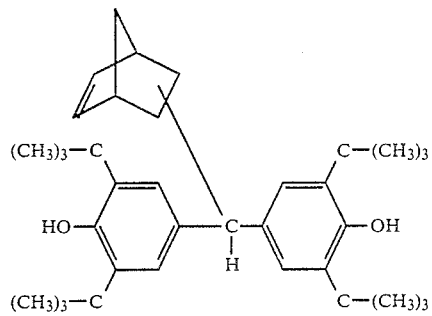

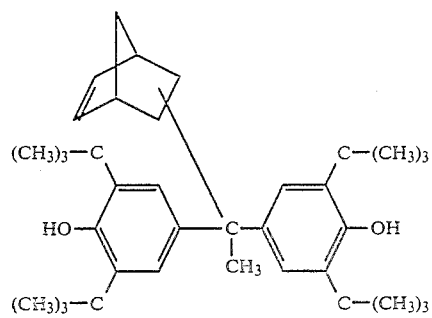

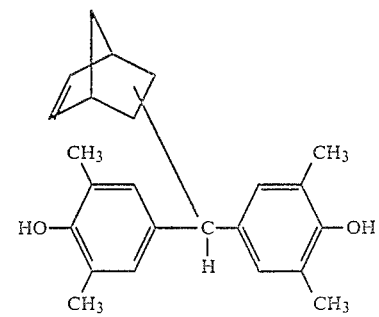

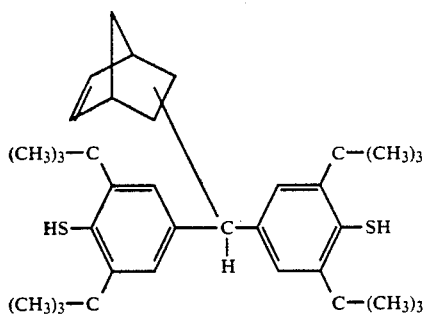

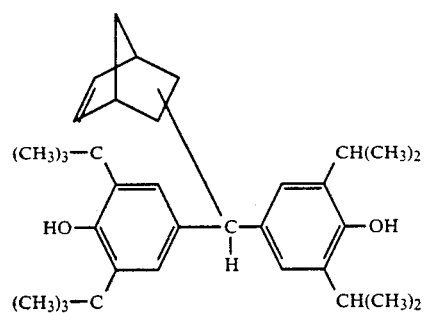

The antioxidants of the present invention are prepared by the base catalyzed condensation reaction of a disubstituted phenol and/or a disubstituted thiophenol with a 2-norbornene carbonyl compound as shown by the following equation:

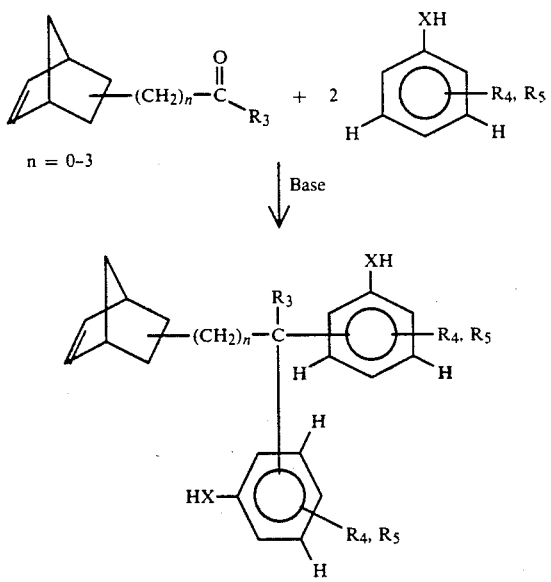

Suitable 2-norbornene carbonyl compounds would include those where $R_3$ is hydrogen or an alkyl group such as methyl, ethyl, propyl, etc. with the carbonyl substitution occurring at any location on the norbornene ring except the double bonded carbons.

Beta,gamma-unsaturated norbornenones such as the structures below:

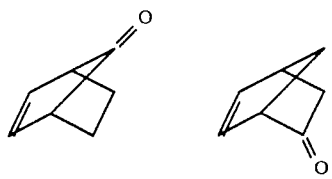

would also be suitable starting materials for the condensation reaction with phenols or thiophenols to yield polymerizable antioxidants of the following structures:

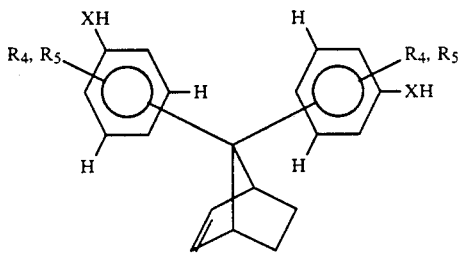

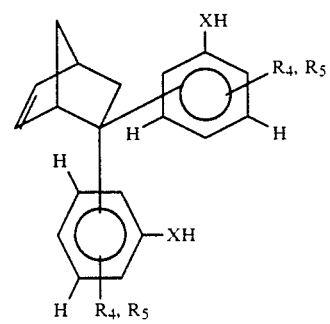

Disubstituted phenols and/or disubstituted thiophenols appropriate for practice of this invention would have $R_4$ and $R_5$ groups each independently alkyl containing 1-8 carbon atoms such as methyl, ethyl, propyl, isopropyl, butyl, t-butyl, pentyl, isopentyl, etc. and with the additional requirement that the $R_4$ and $R_5$ group not be meta to the carbon bearing the oxygen or sulfur atom.

The specific product from the reaction between 2-norbornene-5-carboxyaldehyde and two equivalents of 2,6-di-tert-butylphenol has been named Bisphenol N and is shown as follows:

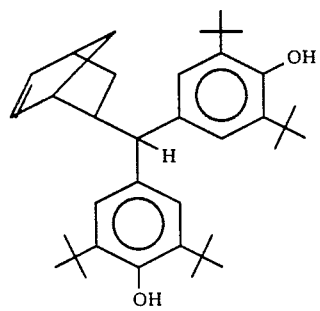

In the case in which two different phenolic and/or thiophenolic groups are substituted on the same norbornene molecule, the corresponding polymerizable antioxidant can be prepared by using an appropriate mixture, typically an equi-molar mixture of the two phenols, thiophenols or mixture of phenol with thiophenol to form the corresponding mixed product.

The reaction is carried out by dissolving the phenol or thiophenol in a lower alkanol solvent such as methyl alcohol followed by the addition of potassium hydroxide in the dissolved state. Then the 2-norbornene-5-carboxaldehyde is added, followed by neutralization and recovery of the desired compound or mixture of compounds.

As will be appreciated by those skilled in the art, if use is made of a mixture of phenols, a mixture of thiophenols or a mixture of a phenol with a thiophenol, then the product will likely be a mixture of compounds in which the norbornene molecule is substituted with mixed phenols and thiophenols.

The Ziegler-polymerizable antioxidants of the present invention find particular utility as comonomers in the Ziegler-polymerization of olefins generally. Thus, the polymerizable antioxidants of the present invention can be copolymerized with ethylene, propylene, butadiene, isoprene and styrene. In addition, the antioxidants of the present invention can be used as comonomers in the polymerization of ethylene with an alpha-olefin containing 3 to 18 carbon atoms, as in the preparation of EPM rubbers and in the copolymerization of ethylene, an alpha-olefin containing 3 to 18 carbon atoms and a non-conjugated diene as in the preparation of EPDM rubbers. Suitable dienes in the preparation of such EPDM polymers include 1,4-hexadiene, monocyclic polyenes and polycyclic polyenes. Representative of such compounds include dicyclopentadiene, octadienes, cyclo-(2,2,1)-hepta, 2,5-diene, the alkylidene norbornenes wherein the alkylidene group contains 1 to 20 carbon atoms and preferable 1 to 8 carbon atoms, the alkenyl norbornenes, and particularly the 5-alkenyl-2-norbornenes wherein the alkenyl group contains about 3 to 20 carbon atoms and preferably 3 to 10 carbon atoms. Other suitable bridged ring polyenes include polyunsaturated derivatives of bicyclo-(2,2,2)-hexane such as bicyclo-(3,2,1)-hexane, polyunsaturated derivatives of bicyclo-(3,3,1)-nonane and polyunsaturated derivatives of bicyclo-(3,2,2)-nonane.

Examples of preferred bridged ring compounds include 5-methylene-2-norbornene, 5-ethylidene-2-norbornene, 5-vinyl-2-norbornene, 5-n-propylidene-2-norbornene, 5-isobutylidene-2-norbornene, 5-n-butylidene-2-norbornene, dicyclopentadiene, 5-(2-methyl-2-butenyl)-2-norbornene, 5-(3-methyl-2-butenyl)-2norbornene and 5-(3,5-dimethyl-4-hexenyl)-2-norbornene.

The EPDM rubbers employing the polymerizable antioxidants of the present invention contain molar ratios of ethylene to propylene (or other of the $C_3$ to $C_{16}$ mono-olefins) varying between 95:1 to 5:90 of ethylene:propylene, and preferably between 85:15 to 55:45 of ethylene:propylene. The polyene or substituted polyene is chemically bound in the EPDM rubber in an amount within the range of 0.1 to 10 mole percent, and preferably 0.3 to 10 mole percent. The polymerizable antioxidant of the present invention is used in an amount ranging from 0.001 to 5 mole percent, depending in part on the particular use to which the polymer is put. The same amount of polymerizable antioxidant can be used in the other polymers as outlined above.

Such polymers are produced in an interpolymerization in the presence of a Ziegler-catalyst well known to those skilled in the art. The techniques for producing such EPM or EPDM interpolymers is well known and is described in U.S. Pat. Nos. 2,9233,480, 3,093,621, 3,211,709, 3,646,168, 3,790,519, 3,884,993, 3,894,999 and 4,059,654, as well as many others.

Typical Ziegler-catalysts are composed of a vanadium compound in which the vanadium is in an oxidation state of +3 or higher, such as $VCl_4$, $VOCl_3$ and many others well known to the art, in combination with an organo-aluminum compound also well known to those skilled in the art.

The polymerizable antioxidants described herein are also usefully employed in copolymerization with ethylene to produce high density polyethylene, including ultra high molecular weight polyethylene and with ethylene and alpha-olefins such as butene, hexene, and octene to produce linear low density polyethylene. Suitable Ziegler-catalysts for the polymerization of ethylene include the combination in any form of a metal alkyl or metal alkyl halide with a transition metal compound of Ti, V, Cr and/or Zr; the transition metal may or may not be supported on an inert carrier such as MgO, $MgCl_2$, silica or alumina. Also suitable in the practice of this invention for producing antioxidant bound polyethylenes is $CrO_3$ supported on activated silica-alumina, also known as the Phillips catalyst.

The polymerizable antioxidant of the present invention is thus copolymerized with the monomer or monomers and serves to impart antioxidant properties to the polymer. One of the advantages of the present invention is that unlike antioxidants which are physically blended with a polymeric composition and have a tendency to migrate through the polymer matrix, the polymerizable antioxidants of the present invention do not undergo such migration because they are chemically bonded to the polymer matrix. The tendency to extract or leach out the antioxidant from fabricated articles where there is fluid contact during end use would also be overcome by practice of this invention.

Having described the basic concepts of the invention, reference is now made to the following examples, which are provided by way of illustration and not by way of limitation, of the practice of the present invention in the preparation of the polymerizable antioxidants of the invention and their use in the interpolymerization with various monomers.

EXAMPLE 1

This example illustrates the preparation and characterization of the condensation product of 2,6-di-5-butylphenol with 2-norbornene-5-carboxaldehyde to yield a product which has been designated Bisphenol N (BPN).

SYNTHESIS OF BISPHENOL N

The reaction is carried out in a 500 ml 3-neck flask equipped with a mechanical stirrer, addition funnel, condenser and heating mantle. The flask was charged with 100 ml reagent methanol containing 5.2 grams dissolved KOH representing 0.08 moles of KOH. This is followed by 41.2 grams (0.2 moles) of 2,6-di-tert-butylphenol. The mixture is placed under nitrogen, warmed gently, and stirred until the phenol dissolves. A solution of 9.8 grams (0.08 moles) of 5-norbornene-2-carboxaldehyde (mixture of isomers) in 20 ml methanol is added dropwise through the addition funnel with stirring. The reaction mixture is heated at the reflux temperature for 16 hours, after which it is allowed to cool to room temperature. A precipitate forms, which can be collected by filtration and washed with fresh methanol. The product is a white powder having a melting point of 203–205° C. A yield of 20.0 grams, representing 48% of the theoretical yield, is obtained.

CHARACTERIZATION OF BISPHENOL N

Bisphenol N is a colorless crystalline solid having a melting point of 203–205° C. The IR spectrum of Bisphenol N exhibits the following absorptions:

| Frequency (cm$^{-1}$) | Relative Abundance | Assignment |
|---|---|---|
| 3660 | med-strong | phenolic O—H |
| 3070 | weak | olefinic/aromatic C—H |
| 2980 | strong | Aliphatic C—H |
| 1560 | weak | C = C |

Peaks in the mass spectrum (solids probe, 70 eV) are listed below:

| Mass | Frequency | Assignment |
|---|---|---|
| 516 | 25% | Molecular ion |
| 423 | 100% | Loss of norbornenyl radical |
| 297 | 10% | Loss of one phenol group |
| 219 | 11% | Tropylium-type ion |
| 93 | 24% | Norbornenyl ion |
| 57 | 98% | t-Butyl ion |

The proton and $^{13}$C NMR spectra of Bisphenol N are consistent with the assigned structure. The NMR data indicate that BPN is a mixture of exo and endo isomers. This is supported by liquid chromatography analysis.
Elemental analysis:
Anal. Calcd. for C$_{36}$H$_{52}$O$_2$;C,83,65; H,10.16;O,6.19
Found: C,83.85;H,10.16;O,5.99 (by difference)

EXAMPLE 2

This example illustrates the interpolymerization of Bisphenol N with ethylene and propylene.

In a typical polymerization, 2.0 milliliters of a solution of 4.09 g recrystallized Bisphenol N in 8.61 g toluene was added to a Sutherland batch reactor containing 4.8 millimoles ethyl aluminum sesquichloride, 0.4 millimoles vanadyl chloride, 0.3 millimoles pyridine and 0.05 millimoles butyl perchorovinylacetate in 900 ml hexane and copolymerized with ethylene and propylene. The reactor temperature was 38° C. and the total pressure on the reactor was 30 psig. The reactor pressure was maintained throughout the run by adding a mixture of 60 percent ethylene and 40 percent propylene. After 20 minutes, the reaction was stopped by killing the catalyst with 1.0 ml isopropyl alcohol and the polymer produced (19.0 grams) was precipitated by adding the reaction mixture t isopropyl alcohol.

The polymer produced in Example 2 was extracted with cyclohexane and acetone to remove any residual monomer and then was examined by means of infrared spectroscopy. The presence of Bisphenol N is indicated by the hydroxyl absorption band at 3610 cm$^{-1}$.

EXAMPLE 3

This example provides the general procedure used for the interpolymerization of ethylene, propylene and ethylidene norbornene.

A pop bottle was filled with 150 ml hexane, 0.8 millimole ethyl aluminum sesquichloride, 0.065 millimole vanadyl chloride, 0.02 millimole butyl perchlorovinylacetate, 0.3 grams ethylidene norbornene and 0.05 millimole pyridine. The reaction pressure was maintained at 30 psig by adding a mixture of 60 percent ethylene and 40 percent propylene. The reaction was carried out at room temperature and stopped after 20 minutes by the addition of isopropyl alcohol.

The following examples illustrate the interpolymerization of Bisphenol N with ethylene, propylene and ethylidene

EXAMPLES 4 TO 7

Polymerizations were carried out as described in Example 3, with the addition of various amounts of Bisphenol N, as 30% solution in toluene. The weight of the total reaction mixture was determined after the run and the solution analyzed for residual Bisphenol N by high pressure liquid chromatography. The results are shown in Table I.

During the course of the chromatographic analysis it was noticed that the standard solutions of the Bisphenol N monomer exhibited two peaks, which may be related to two isomers of Bisphenol N. The ratio of the area of these two peaks in the starting material ranged from 1.05 to 1.09. The higher ratio in the residual Bisphenol N after polymerization may indicate that the two isomers polymerize at different rates.

TABLE I

Residual Bisphenol N After Polymerization

| | Bisphenol N | | | | |
|---|---|---|---|---|---|
| Example | Polymer Grams | Added mg | Residual ppm | Wt % Bound In Polymer | Residual Monomer Isomer Ratio |
| 3 | 2.70 | 0 | 0 | 0 | — |
| 4 | 2.41 | 20 | 10 | 0.78 | 1.49 |
| 5 | 2.46 | 40 | 20 | 1.13 | 1.61 |
| 6 | 2.35 | 80 | 55 | 3.22 | 1.52 |
| 7 | 2.74 | 100 | 100 | 5.43 | 1.46 |

EXAMPLE 8

This example provides the general procedure used for Synthesis of an analog of Bisphenol N.

The reaction was carried out in a 200 ml three neck roundbottom flask equipped with a condenser, mechanical stirrer, and rubber septum. The flask was charged with 50 ml reagent methanol, 5.2 grams (0.08 mole) KOH pellets, and 24.4 grams (0.2 mole) 2,6-dimethylphenol. A nitrogen atmosphere was set up by admitting nitrogen through the septum and letting it exit through the condenser, via a bubbler containing mineral oil. 5-Norbornene-2-carboxyaldehyde (9.8 grams, 0.08 moles) was added via syringe through the septum. The reaction mixture was heated at the reflux temperature with stirring for sixteen hours. Upon cooling, the product remained in solution. The solution was neutralized with 4 molar HCl to pH 5–7. The mixture was diluted with 100 ml dichloromethane. This was washed three times in a separatory funnel with 30 ml portions of fresh water. The solution was dried over magnesium sulfate. After filtration to remove the drying agent, the solution was evaporated to provide 27.5 grams of a solid residue. This was purified by column chromatography (silica gel, 1/1 hexane/dichloromethane) to yield 16.5 grams of product representing a 59% yield. Recrystallization from toluene provided colorless crystals which had a melting point of 176–178° C. This product is the Bisphenol N analog having methyl groups substituted on the phenol rings in place of the t-butyl groups.

I claim:

1. A compound having the formula:

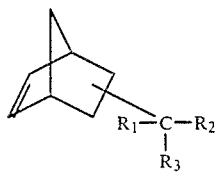

wherein $R_1$ and $R_2$ are each an aryl group imparting antioxidant properties to the compound, and $R_3$ is hydrogen or an alkyl group.

2. A compound having the formula:

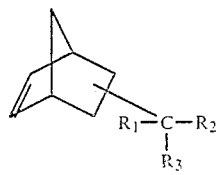

wherein $R_1$ has the formula:

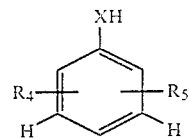

and $R_2$ has the formula:

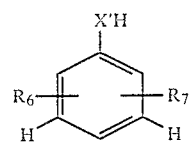

wherein $R_4$, $R_5$, $R_6$ and $R_7$ are each selected from the group consisting of alkyl containing 1 to 8 carbon atoms, X and X' are each -O- or -S-, and $R_3$ is hydrogen or an alkyl group.

3. A compound as defined in claim 2 wherein $R_4$, $R_5$, $R_6$ and $R_7$ are each t-butyl.

4. A compound as defined in claim 2 wherein $R_4$, $R_5$, $R_6$ and $R_7$ are each methyl.

5. A compound as defined in claim 2 wherein $R_4$, $R_5$, $R_6$ and $R_7$ are each isopropyl.

6. A compound as defined in claim 2 wherein X and X' are each O.

7. A compound as defined in claim 2 wherein $R_1$ and $R_2$ are each a group having the formula:

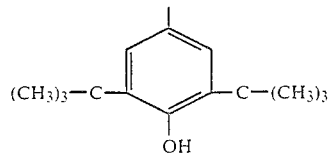

8. The compound Bisphenol N.

* * * * *